United States Patent
Falco

(10) Patent No.: US 6,720,172 B1
(45) Date of Patent: Apr. 13, 2004

(54) GENES ENCODING SULFATE ASSIMILATION PROTEINS

(75) Inventor: Saverio Carl Falco, Arden, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/720,524

(22) PCT Filed: Jul. 13, 1999

(86) PCT No.: PCT/US99/15812

§ 371 (c)(1),
(2), (4) Date: Dec. 21, 2000

(87) PCT Pub. No.: WO00/04162

PCT Pub. Date: Jan. 27, 2000

Related U.S. Application Data

(60) Provisional application No. 60/092,833, filed on Jul. 14, 1998.

(51) Int. Cl.$^7$ ............... C12N 9/02; C12N 15/00; C12N 5/04; C12N 15/82; C07H 21/04

(52) U.S. Cl. ............... 435/189; 435/320.1; 435/419; 435/468; 435/325; 435/252.3; 435/440; 536/23.2

(58) Field of Search ............... 435/189, 320.1, 435/6, 252.33, 69.1, 419, 468, 325, 440; 536/23.2; 800/278, 295

(56) References Cited

PUBLICATIONS

EMBL sequence library data accession No. AY017473, Feb. 4, 2001, bases 1–1801, cDNA sequence for soybean ferrodoxin:sulfite reductase, unpublished, Keaton M. A. et al.*
EMBL Sequence Library Data Accession No. D89631, Jul. 30,, 1997, Sohlberg, L.E. et al., Nucleoside Sequence of a cDNA encoding a Cys proteinase from germinating bean cotyledons, XP–0021299910.
EMBL Sequence Library Data Accession No. 049307, Jun. 1, 1998, Federspiel, N.A. et al., XP–002129911.
EMBL Sequence Library Data Accession No. D25000, Nov. 30, 1993, Minobe, Y. et al., Rice cDNA from root, XP–002129912.
Frank W. Smith et al., PNAS, vol. 92–9373–9377, Sep. 1995, Plant members of a family of sulfate transporters reveal functional subtypes, XP–002129913.
Hideki Takahashi et al., Plant & Cell Phys., vol. 39 suppl, pp. S148, 1998, Antisense repression of sulfate transporter in transgenic Arabidopsis thaliana plants, XP–002121793.
Hideki Takahashi et al., PNAS, vol. 94:11102–11197, Sep. 1997, Regulation of sulfur assimilation in higher plants: A sulfate trnasporter induced in sulfate–starved roots plays a central role in Arabidopsis thaliana.
EMBL Sequence Library Data Accession No. X96761, Mar. 25, 1997, NG, A. et al., Isolation & characterization of a lowly expressed cDNA from the resurrection grass Sporobolus stapfianus with homology to eukaryote sulfate transporter proteins, XP–002121791.
EMBL Sequence Library Data Accession No. AF016306, Jan. 8, 1998, Bolchi, A. et al., Coordinate modulation of maize sulfate permease and ATP sulfate permease and ATP sulfurylase mRNAs in response to variations in sulfur nutritional status: stereospecific down–regulation by L–cysteine, XP–002121790.
EMBL Sequence Data Library Accession No. O48889, Jun. 1, 1998, Bolchi, A. et al.
Frank W. Smith et al., The Plant Journal, vol. 12(4):875–884, 1997, Regulation of expression of a cDNA from barley roots encoding a high affinity sulphate transporter, XP–002129909.
Antje Prior et al., Biochimica et Biophysica Acta, vol. 1430:25–38, 1999, Structural and kinetic properties of adenylyl sulfate reductase from Catharanthus roseus cell cultures.
Senta Heiss et al., Plant Mol. Biol., vol. 39:847–857, 1999, Cloning sulfur assimilation genes of Brassica juncea L.: cadmium differentially affects the expression of a putative low–affinity sulfate transporter and isoforms of ATP sulfurylase and APS reductase.
John L. Wray et al., Chemico–Biological Interactions, vol. 109:153–167, 1998, Redefining reductive sulfate assimilation in higher plants: a role for APS reductase, a new member of the thioredoxin superfamily?
Julie–Ann Bick et al., PNAS, vol. 95:8404–8409, Jul. 1998, Glutaredoxin function for the carboxyl–terminal domain of the plant–type 5'–adenylsulfate reductase.
Jose F. Gutierrez–Marcos et al., PNAS, vol. 93:13377–13382, 1996, Three members of a novel small gene–family from Arabidopsis thaliana able to complement funtionally an Escherichia coli mutant defective in PAPS reductase activity encode proteins with a thioredoxin–like domain and "APS reductase" activity.
Amit Setya et al., PNAS, vol. 93:13383–13388, 1996, Sulfate reduction in higher plants: Molecular evidence for a novel 5'–adenylylsulfate reductase.
EMBL Sequence Library Data Accession No. C27405, Aug. 6, 1997, Sasaki, T. et al., Rice cDNA from callus, XP–002121812.

(List continued on next page.)

Primary Examiner—Rebecca E. Prouty
Assistant Examiner—Malgorzata A. Walicka

(57) ABSTRACT

This invention relates to an isolated nucleic acid fragment encoding a sulfate assimilation protein. The invention also relates to the construction of a chimeric gene encoding all or a portion of the sulfate assimilation protein in sense or antisense orientation, wherein expression of the chimeric gene results in production of altered levels of the sulfate assimilation protein in a transformed host cell.

11 Claims, 4 Drawing Sheets

OTHER PUBLICATIONS

EMBL Sequence Library Data Accession No. AF071890, Jun. 29, 1998, Mbeguie–A–Mbeguie D. et al., Molecular cloning and partial nucleotide sequence of a sulfite reductase from apricot fruit, XP–002128211.

EMBL Sequence Library Data Accession No. D50679, Dec. 1, 1997, Ideguchi, T. et al., cDNA cloning and functional expression of ferredoxin–dependent sulfate reductase from miaze in *E. coli* cells, XP–002128212.

Christine Bork et al., Gene, vol. 212:147–153, 1998, Isolation and characterization of a gene for assimiliatory sulfite reductase from *Arabidopsis thaliana*.

Andreas Bruhl et al., Biochimia et Biophysica Acta, vol. 1295: 119–124, 1996, A cDNA clone from *Arabidopsis thaliana* encoding plastidic ferredoxin: sulfite reductase.

Database WPI, Derwent Publ., Ltd., JP–62 455773, Mitsubishi Corp., Sep. 6, 1994, XP–002121814.

EMBL Sequence Library Data Accession No. AU068082, Jun. 7, 1999, Sasaki, T. et al., Rice cDNA from callus, XP–002128630.

EMBL Sequence Library Data Accession No. AQ688702, Jul. 2, 1999, Yu, Y. et al., A Bac Encd sequencing framework to sequence the rice genome, XP–002128631.

Saito, K., Stress Responses of Photosynthetic organisms, 1996, pp. 215–226, Molecular Aspects of Sulfur Assimilation and Acclimiation to Sulphur Supply in Plants.

Kazuki Saito et al., Plant Phys., vol. 106:887–895, 1994, Moedulation of Cystine Biosynthesis in Chloroplasts of Transgenic Tobacco Overexpressing Cystein Synthase [O–Acetylserine(thiol)–lyase][1].

Kazuki Saito et al., Comptes Rendu De L'Academie Des Sciences, vol. 319:969–973, 1996, Molecular characterization of cysteine biosynthetic enzymes in plants.

Yoo, B. et al., Plant Phys. suppl., vol. 114:267, 1997, Regulation of recombinant soybean serine acetyltransferase by CDPK.

EMBL Sequence Library Data Accession No. p93544, May 1, 1997, Saito, K. et al., XP–002128628.

EMBL Sequence Library Data Accession No. C26373, Aug. 6, 1997, Sasaki, T. Rice cDNa from callus, XP–002128627.

Michael A. Roberts et al., Plant Molecular biology, vol. 30:1041–1049, Cloning and characterisation of an *Arabidopsis thialiana* cDNa clone encoding an organellar isoform of serine acetyltransferase.

Kazuki Saito et al., Journ. of Biol. Chem., vol. 270(2):16321–16326, 1995, Molecular cloning and characterization of a Plant Serine acetyltransferase playing a regulatory role in cystein biosynthesis from watermelon.

EMBL Sequence Data Library Accession No. AI637166, Apr. 27, 1999, Walbot, V., Maize ESTs from various cDNA libraries sequenced at Stanford University, XP–002123195.

Sangman Lee et al., Biochem. and Biophys. Res. Comm., vol. 247:171–175, 1998, APS Kinase from *Arabidopsis thaliana*: Genomic Organization, Expression, and Kinetic Analysis of the Recombinant Enzyme.

Ajay Jain et al., Plant Phys., vol. 105:771–772, 1994, A cDNA clone for 5'–Adenylylphosphosulfate Kinase from *Arabidopsis thaliana*.

Sandra Schiffmann et al., FEBS Lett., vol. 355:229–232, 1994, APS–sulfotransferase activity is identical to higher plant APS–kinase.

Julie Ann Bick et al., Current Opinion in Plant Biology, vol. 1(3):240–244, 1998, Plant sulfur metabolism—the reduction of sulfate to sulfite.

Hildegard E. Arz et al., Biochimica et Biophysica Acta., vol. 1218:447–452, 1994, A cDNA for adenylyl sulphate (APS)–kinase from *Arabidopsis thaliana*.

National Center for Biotechnology Information General Identifier No. 3721540, Feb. 6, 1999, Yonekura–Sakakibara, K. et al., Molecular characterization of tobacco sulfite reductase: enzyme prufication, gene cloning, and gene expression analysis.

National Center for Biotechnology Information General Identifier No. 2653558, Feb. 1, 2000, Ideguchi, T. et al., cDNa cloning and functional expression of ferredoxin–dependent sulfite reductase from maize in *E. coli* cells.

Amit Setya et al., PNAS, vol. 93:13383–13388, Nov. 1996, Sulfate reduction in higher plants: Molecular evidence for a novel 5'adenylylsulfate reductase.

Kazuki Saito et al., Journ. of Biol. Chem., vol. 270(27):16321–16326, 1995, Molecular cloning and characterization of a Plant serine acetyltransferase playing a regulatory role in cystein biosynthesis from watermelon.

Frank W. Smith et al., PNAS, vol. 92:9373–9377, Sep. 1995, Plant members of a family of sulfate transporters reveal functional subtypes.

Angelo Bolchi et al., Plant Mol. biol., vol. 39:527–537, 1999, Coordinate moedulation of maize sulfate permease and ATP sulfurylase mRNAs in response to variations in sulfur nutritional status: stereospecific down–regulation by L–cystein.

Keiko Yonekura–Sakakibara et al., J. Biochem., vol. 124:615–621, 1998, Molecular characterization of tobacco sulfite reductase: enzyme purification, gene cloning, and gene expression analysis.

* cited by examiner

```
                       1                                                            60
SEQ ID NO:2    TRKRKYPTREDTLFPFFSRRKPRAKAPTPTPVMSAAVGGAEFHGFRGGGGAAQLQRSRM
SEQ ID NO:4    M-----TTSFG---------------PATTSAPLKDH--KVQIPSFHGLRSSSASALPRNA
SEQ ID NO:6    ------------------------------------------------------------
SEQ ID NO:7    ---------------------------------MSGAIGGAEVHGFRGA---AAQLPRSRV
SEQ ID NO:8    M-----TTSFG-----------------AAINIAVADDPNPKLQIHNFSGLKSTSNSLLLSRR 61                                                           120
SEQ ID NO:2    LGRPLRVATPHAAAPAGGGGSSSASIRAVSAPLKKDASEVKRSKVEIIKEKSNFLRYPLN
SEQ ID NO:4    LSLP---SSTR--------SLSLIRAVSTPAQSETATVKRSKVEIFKEQSNFIRYPLN
SEQ ID NO:6    ------------------------------------------------------------
SEQ ID NO:7    LGRPIRVAPPAAARP---GGASAGSIRAVSAPAKKDASEVKRSKVEIIKEKSNFLRYPLN
SEQ ID NO:8    LHVFQSFSPSN---------PSSIVRAVSTPAKPAAVEPKRSKVEIFKEQSNFIRYPLN 121                                                          180
SEQ ID NO:2    EELVSEAPNINDSAVQLIKFHGSYQQTDRDVRGQKNYSFMLRTKNPCGKVPNQLYLAMDT
SEQ ID NO:4    EDILTDAPNISEAATQLIKFHGSYQQYNREERGSRSYSFMIRTKNPCGKVSNQLYLTMDD
SEQ ID NO:6    ------------------------------------------------------------
SEQ ID NO:7    EELVSEAPNINESAVQLIKFHGSYQQTDRDVRGQKNYSFMLRTKNPCGKVPNQLYLAMDT
SEQ ID NO:8    EEILNDAPNINEAATQLIKFHGSYMQYDRDERGGRSYSFMLRTKNPGGEVPNRLYLVMDD 181                                                          240
SEQ ID NO:2    LADEFGIGTLRLTTRQTFQLHGVLKKNLKTVISTVIKNMGSSLGACGDLNRNVLAPAAPY
SEQ ID NO:4    LADQFGIGTLRLTTRQTFQLHGVLKKDLKTVMGTIIRNMGSTLGACGDLNRNVLAPAAPL
SEQ ID NO:6    ------LRLTTRQTFQLHGVLKKNLKTVLSTVIKNMGSTLGACGDLNRNVLAPAAPY
SEQ ID NO:7    LADEFGIGTLRLTTRQTFQLHGVLKKNLKTVLSTVIKNMGSTLGACGDLNRNVLAPAAPY
SEQ ID NO:8    LADQFGIGTLRLTTRQTFQLHGVLKKNLKTVMSTIIKNMGSTLGACGDLNRNVLAPAAPF
```

FIG. 1A

```
                  241                                                                      300
SEQ ID NO:2       VRKDILFAQETAENIAALLTPQSGAYYDLWVDGEKIMSAEEPPEVTKARNDNTYGTNFPD
SEQ ID NO:4       ARKDYLFAQQTAENIAALLAPQSGFYYDIWVDGEKILTSE-PPEVVQARNDNSHGTNFPD
SEQ ID NO:6       ------------------------------------------------------------
SEQ ID NO:7       VKKDILFAQQTAENIAALLTPQSGAYYDLWVDGEKIMSAEEPPEVTKARNDNSHGTNFPD
SEQ ID NO:8       AKKDYMFAKQTADNIAALLTPQSGFYYDVWVDGEKVMTAE-PPEVVKARNDNSHGTNFPD 301                                                                      360
SEQ ID NO:2       SPEPIYGTQYLPRKFKIAVTVAGDNSVDILTNDIGVVVSDSAGEPVGFNIYVGGGMGRT
SEQ ID NO:4       SPEPIYGTQFLPRKFKIAVTVPTDNSVDILTNDIGVVVVTDDDGEPQGFNIYVGGGMGRT
SEQ ID NO:6       ------------------------------------------------------------
SEQ ID NO:7       SPEPIYGTQYLPRKFKVAVTAAGDNSVDILTNDIGVVVSDDAGEPIGFNIYVGGGMGRT
SEQ ID NO:8       SPEPIYGTQFLPRKFKIAVTVPTDNSVDIFTNDIGVVVSNEDGEPQGFNIYVGGGMGRT 361                                                                      420
SEQ ID NO:2       HRVETTFPRLADPLGYVPKEDILYAIKAIVVTQRENGRRDDRRYSRMKYLIDNWGIEKFR
SEQ ID NO:4       HRLETTFPRLAEPIGYVPKEDILYAVKAIVVTQRENGRRDDRKYSRLKYLISSWGIEKFR
SEQ ID NO:6       ------AIVVTQRENGRRDDRRYSRLKYLLDSWGIDKFR
SEQ ID NO:7       HRVETTFPRLADPLGYVPKEDILYAIKAIVVTQRENGRRDDRKYSRMKYMIDRWGIDRFR
SEQ ID NO:8       HRMETTFPRLAEPLGYVPKEDILYAVKAIVVTQRENGRRDDRRYSRLKYLLSSWGIEKFR 421                                                                      480
SEQ ID NO:2       AEVEKYYGKKFEDSRPLPEWQFNSYLGWQEQGDGKLFYGVHVDNGRVAGQAKKTLREIIE
SEQ ID NO:4       SVVEQYYGKKFEPFRALPEWEFKSYLGWHEQGDGKLFYGLHVDNGRIGGNMKKTLREVIE
SEQ ID NO:6       AEAEKYYGKKFEDFRPLPEWQFNSYLGWQEQGDGKLFYGVHVDNGRLGGQAKKTLREIIE
SEQ ID NO:7       AEVEKYYGKKFESFRPLPEWQFNSYLGWQEQGDGKLFYGVHVDNGRVGGQAKKTLREIIE
SEQ ID NO:8       SVTEQYYGKKFQPCRELPEWEFKSYLGWHEAGDGSLFCGLHVDNGRVKGAMKKALREVIE
```

FIG. 1B

```
              481
SEQ ID NO:2   KYNLEVSITPNQNLILCGIDQAWKDPITAALAQSGLLEPKDVDPLNITSMACPALPLCPL
SEQ ID NO:4   KYNLNVRITPNQNILLTDVRAAWKRPITTLAQAGLLQPRFVDPLNITAMACPAFPLCPL
SEQ ID NO:6   KYSLDVSITPNQNLILCGVDQAWREPITAALAQAGLLEPKDVDLLNITSMACPALPLCPL
SEQ ID NO:7   KYNLDVSITPNQNLILCGIDQAWREPITTALAQAGLLEPKDVDPLNLTAMACPALPLCPL
SEQ ID NO:8   KYNLNVRLTPNQNIILCNIRQAWKRPITTVLAQGLLQPRYVDPLNLTAMACPAFPLCPL
                                                                    540

541
SEQ ID NO:2   AQTEAERGILPILKRIRAVEDKVGIKDHESVVVRITGCPNGCARPYMAEVGFVGDGPNSY
SEQ ID NO:4   AITEAERGIPNILKRIRDVFDKVGLKYSESVVVRITGCPNGCARPYMAELGLVGDGPNSY
SEQ ID NO:6   AQTEAERGILPILKRIRAVEDKVGIKDEESVVVRITGCPNGCARPYMAEVGFVGDGPNSY
SEQ ID NO:7   AQTEAERGILPILKRIRAVENKVGIKDSESVVVRITGCPNGCARPYMAELGFVGDGPKSY
SEQ ID NO:8   AITEAERGIPDILKRVRAIFERVGLKYSESVVIRITGCPNGCARPYMAELGLVGDGPNSY
                                                                    600

601
SEQ ID NO:2   QIWLGGTPNQSTLAETFMNKVKLQDIEKVLEPLFSYWNSTRQEGESFGSFTRRTGFDKLK
SEQ ID NO:4   QIWLGGNHKQTSLARSFMDRVKILDLEKVLEPLFYYWKQKRQSKESFGDFTNRMGFEKLK
SEQ ID NO:6   QIWLGGTPNQTTLAETFMNKVKLQDIEKVLEPLFSYWNSTRQEGESFGSFTNRMGFEQLK
SEQ ID NO:7   QIWLGGTPNQSTLAESFMDKVKLDDIEKVLEPLFTYWNGTRQEGESFGSFTNRTGFDKLK
SEQ ID NO:8   QIWLGGTPNQTSLAKTFKDKLKVQDLEKVLEPLFFHWRRKRQSKESFGDFTNRMGFEKLG
                                                                    660
```

FIG. 1C

```
              661                                                            720
SEQ ID NO:2   EVVNKWAESASAA------------------------------------------------
SEQ ID NO:4   EYIEKWEGPVVAPSRHNLKLFADKETYESMDALAKLQNKTAHQLAMEVIRNYVASNQNGK
SEQ ID NO:6   EVVNKWEGSASAA------------------------------------------------
SEQ ID NO:7   EVVNKWAESPSAA------------------------------------------------
SEQ ID NO:8   EFVEKWEGIPESSSRYNLKLFADRETYEAMDALASIQDKNAHQLAIEVVRNYVASQQNGK

721
SEQ ID NO:2   ---
SEQ ID NO:4   G-E
SEQ ID NO:6   ---
SEQ ID NO:7   ---
SEQ ID NO:8   SMD
```

FIG. 1D

GENES ENCODING SULFATE ASSIMILATION PROTEINS

This application claims the benefit of U.S. Provisional Application No. 60/092,833, filed Jul. 14, 1998.

FIELD OF THE INVENTION

This invention is in the field of plant molecular biology. More specifically, this invention pertains to nucleic acid fragments encoding sulfate assimilation proteins in plants and seeds.

BACKGROUND OF THE INVENTION

Sulfate assimilation is the process by which environmental sulfur is fixed into organic sulfur for use in cellular metabolism. The two major end products of this process are the essential amino acids cysteine and methionine. These amino acids are limiting in food and feed; they cannot be synthesized by animals and thus must be acquired from plant sources. Increasing the level of these amino acids in feed products is thus of major economic value. Key to that process is increasing the level of organic sulfur available for cysteine and methionine biosynthesis.

Multiple enzymes are involved in sulfur assimilation. These include: High affinity sulfate transporter and low affinity sulfate transporter proteins which serve to transport sulfur from the outside environment across the cell membrane into the cell (Smith et al. (1995) PNAS 92(20):9373–9377). Once sulfur is in the cell sulfate adenylyltransferase (ATP sulfurylase) (Bolchia et al. (1999) Plant Mol. Biol. 39(3):527–537) catalyzes the first step in assimilation, converting the inorganic sulfur into an organic form, adenosine-5' phosphosulfate (APS). Next, several enzymes further modify organic sulfur for use in the biosynthesis of cysteine and methionine. For example, adenylylsulfate kinase (APS kinase), catalyzes the conversion of APS to the biosynthetic intermediate PAPS (3'-phospho-adenosine-5' phosphosulfate) (Arz et al. (1994) Biochim. Biophy. Acta 1218(3):447–452). APS reductase (5' adenylyl phosphosulphate reductase) is utilized in an alternative pathway, resulting in an inorganic but cellularly bound (bound to a carrier), form of sulfur (sulfite) (Setya et al. (1996) PNAS 93(23):13383–13388). Sulfite reductase further reduces the sulfite, still attached to the carrier, to sulfide and serine O-acetyltransferase converts serine to O-acetylserine, which will serve as the backbone to which the sulfide will be transferred to from the carrier to form cysteine (Yonelcura-Sakakibara et al. (1998) J. Biolchem. 124(3):615–621 and Saito et al. (1995) J. Biol. Chem. 270(27):16321–16326).

As described, each of these enzymes is involved in sulfate assimilation and the pathway leading to cysteine biosynthesis, which in turn serves as an organic sulfur donor for multiple other pathways in the cell, including methionine biosynthesis. Together or singly these enzymes and the genes that encode them have utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

SUMMARY OF THE INVENTION

The instant invention relates to isolated nucleic acid fragments encoding sulfate assimilation proteins. Specifically, this invention concerns an isolated nucleic acid fragment encoding a sulfite reductase and an isolated nucleic acid fragment that is substantially similar to an isolated nucleic acid fragment encoding a sulfite reductase. In addition, this invention relates to a nucleic acid fragment that is complementary to the nucleic acid fragment encoding sulfite reductase. An additional embodiment of the instant invention pertains to a polypeptide encoding all or a substantial portion of a sulfite reductase.

In another embodiment, the instant invention relates to a chimeric gene encoding a sulfite reductase, or to a chimeric gene that comprises a nucleic acid fragment that is complementary to a nucleic acid fragment encoding a sulfite reductase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a sulfite reductase, operably linked to suitable regulatory sequences. Expression of the chimeric gene results in production of altered levels of the encoded protein in the transformed host cell. The transformed host cell can be of eukaryotic or prokaryotic origin and include cells derived from higher plants and microorganisms. The invention also includes transformed plants that arise from transformed host cells of higher plants, and seeds derived from such transformed plants.

An additional embodiment of the instant invention concerns a method of altering the level of expression of a sulfite reductase in a transformed host cell comprising: a) transforming a host cell with a chimeric gene comprising a nucleic acid fragment encoding a sulfite reductase; and b) growing the transformed host cell under conditions that are suitable for expression of the chimeric gene wherein expression of the chimeric gene results in production of altered levels of sulfite reductase in the transformed host cell.

An addition embodiment of the instant invention concerns a method for obtaining a nucleic acid fragment encoding all or a substantial portion of an amino acid sequence encoding a sulfite reductase.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIGS. 1A–1D show a comparison of the amino acid sequences set forth in SEQ ID NOs:2, 4 and 6 and the Zea mays and Nicotiana tabacum sequences (SEQ ID NOs:7 and 8 respectively).

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Sulfate Assimilation Proteins

| Protein | Clone Designation | SEQ ID NO: (Nucleotide) | SEQ ID NO: (Amino Acid) |
|---|---|---|---|
| Sulfite Reductase | rlr12.pk0027.d1 | 1 | 2 |
| Sulfite Reductase | srm.pk0035.h7 | 3 | 4 |
| Sulfite Reductase | Contig composed of:<br>wdk3c.pk006.11<br>wlm96.pk0012.h1<br>wlm96.pk028.g9<br>wrl.pk180.b10 | 5 | 6 |

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "nucleic acid fragment" is a polymer of RNA or DNA that is single- or double-stranded, optionally containing synthetic, non-natural or altered nucleotide bases. A nucleic acid fragment in the form of a polymer of DNA may be comprised of one or more segments of cDNA, genomic DNA or synthetic DNA.

As used herein, "contig" refers to a nucleotide sequence that is assembled from two or more constituent nucleotide sequences that share common or overlapping regions of sequence homology. For example. the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-á-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Moreover, substantially similar nucleic acid fragments may also be characterized by their ability to hybridize, under stringent conditions (0.1×SSC, 0.1% SDS, 65° C.), with the nucleic acid fragments disclosed herein.

Substantially similar nucleic acid fragments of the instant invention may also be characterized by the percent identity of the amino acid sequences that they encode to the amino acid sequences disclosed herein, as determined by algorithms commonly employed by those skilled in this art. Preferred are those mucleic acid fragments whose nucleotide sequences encode amino acid sequences that are 95% identical to the amino acid sequences reported herein. Sequence alignments and percent identity calculations were performed using the Megalign program of the LASARGENE bioinformatics computing suite (DNASTAR Inc. Madison, Wis.). Muliple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410). In general, sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Molecular Biotechnology* 3:225).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expressions", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 (hereinafter "Maniatis").

Nucleic acid fragments encoding at least a portion of a sulfate assimilation protein have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction ligase chain reaction).

For example, genes encoding other sulfite reductase enzymes, either as cDNAs or genomic DNAs could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673; Loh et al. (1989) *Science* 243:217). Products generated by the 3' and 5' RACE procedures can be combined to generate full-length cDNAs (Frohman and Martin (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of sulfite reductase in those cells. This enzyme is involved in sulfate assimilation and the pathway leading to cysteine biosynthesis, which in turn serves as an organic sulfur donor for multiple other pathways in the cell. including methionine biosynthesis. This enzyme and the gene(s) that encodes the protein has utility in overcoming the sulfur limitations known to exist in crop plants. It may be possible to modulate the level of sulfur containing compounds in the cell, including the nutritionally critical amino acids cysteine and methionine. Specifically, their overexpression using tissue specific promoters will remove the enzyme in question as a possible limiting step, thus increasing the potential flux through the pathway to the essential amino acids. This will allow the engineering of plant tissues with increases levels of these amino acids, which now often must be added a supplements to animal feed.

Overexpression of the proteins of the instant invention may be accomplished by first constructing a chimeric gene in which the coding region is operably linked to a promoter capable of directing expression of a gene in the desired tissues at the desired stage of developrment. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.*100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppresion technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention iii situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded sulfate assimilation protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet.* 7:149–154). Although current methods of FISH mapping favor use of large clones (several to several hundred KB; see Laan et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med.* 114(2):95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nature Genetics* 7:22–28) and Happy Mapping (Dear and Cook (1989) *Nucleic Acid Res.* 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402; Koes et al. (1995) *Proc. Natl. Acad. Sci USA* 92:8149; Bensen et al. (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptides. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries: Isolation and Sequencing of cDNA Clones cDNA libraries representing mRNAs from various rice, soybean and wheat tissues were prepared. The characteristics of the libraries are described below.

TABLE 2 cDNA Libraries from Rice, Soybean and Wheat

| Library | Tissue | Clone |
|---|---|---|
| rlr12 | Rice (*Oryza sativa* L.) leaf (15 days after germination) 12 hours after infection of *Magaporthe grisea* strain 4360-R-62 (AVR2-YAMO); Resistant | rlr12.pk0027.d1 |
| srm | Soybean (*Glycine max* L.) root meristem | srm.pk0035.h7 |
| wdk3c | Wheat (*Triticum aestivum* L.) developing kernel, 14 days after anthesis | wdk3c.pk006.11 |
| wlm96 | Wheat (*Triticum aestivum* L.) seedlings 96 hr after inoculation w/*E. graminis* | wlm96.pk0012.h1 wlm96.pk028.g9 |
| wr1 | Wheat (*Triticum aestivum* L.) root; 7 day old seedling, light grown | wr1.pk180.b10 | cDNA libraries may be prepared by any one of many methods available. For example, the cDNAs may be introduced into plasmid vectors by first preparing the cDNA libraries in Uni-ZAP* XR vectors according to the manufacturer's protocol (Stratagene Cloning Systems, La Jolla, Calif). The Uni-ZAP* XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651). The resulting ESTs are analyzed using a Perkin Elmer Model 377 fluorescent sequencer.

Example 2

Identification of cDNA Clones cDNA clones encoding sulfate assimilation proteins were identified by conducting BLAST (Basic Local Alignment Search Tool; Altschul et al. (1993) *J. Mol. Biol.* 215:403–410) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Sulfite Reductase

The BLASTX search using the EST sequences from clones listed in Table 3 revealed similarity of the polypeptides encoded by the cDNAs to sulfite reductase from *Zea mays* (NCBI Identifier No. gi 2653558) and *Nicotiana tabacum* (NCBI Identifier No. gi 3721540). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Zea mays* and *Nicotiana tabacum* Sulfite Reductase

| Clone | Status | BLAST pLog Score |
|---|---|---|
| rlr12.pk0027.d1 | FIS | >254.00 (gi 2653558) |
| srm.pk0035.h7 | FIS | >254.00 (gi 3721540) |
| Contig composed of: wdk3c.pk006.11 wlm96.pk0012.h1 wlm96.pk028.g9 wr1.pk180.b10 | Contig | >254.00 (gi 2653558) |

FIGS. 1A–1D present an alignment of the amino acid sequences set forth in SEQ ID NOs:2, 4 and 6 and the *Zea mays* and *Nicotiana tabacum* sequences (SEQ ID NOs:7 and 8 respectively). The data in Table 4 represents a calculation of the percent identity of the amino acid sequences set forth in SEQ ID NOs:2, 4 and 6 and the *Zea mays* and *Nicotiana tabacum* sequences (SEQ ID NOs:7 and 8).

TABLE 4

Percent Identity of Amino Acid Sequences Deduced From the Nucleotide Sequences of cDNA Clones Encoding Polypeptides Homologous to *Zea mays* and *Nicotiana tabacum* Sulfite Reductase

| SEQ ID NO. | Percent Identity to |
|---|---|
| 2 | 91% |
| 4 | 80% |
| 6 | 89% |

Sequence alignments and percent identity calculations were performed using the Megalign program of the LASAR- GENE bioinformatics computing suite (DNASTAR Inc., Madison, Wis.). Multiple alignment of the sequences was performed using the Clustal method of alignment (Higgins and Sharp (1989) *CABIOS.* 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignments and BLAST scores and probabilities indicate that the nucleic acid fragments comprising the instant cDNA clones encode a substantial portion of a sulfite reductase. These sequences represent the first corn, rice, soybean and wheat sequences encoding sulfite reductase.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb Ncol-SmaI fragment of the plasmid pML 103. Plasmid pML 103 has been deposited under the terms of the Budapest Treaty at ATCC (American Type Culture Collection, 10801 University Blvd., Manassas, Va. 20110-2209), and bears accession number ATCC 97366.The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Pat. Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens.*

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/ He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.*

261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment the liquid media may be exchanged with fresh media, and eleven to twelve days post bombardment with fresh media containing 50 mg/mL hygromycin. This selective media can be refreshed weekly. Seven to eight weeks post bombardment, green transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430.This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methyl-sulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having sulfite reductase activity, wherein the polypeptide has an amino acid sequence of at least 95% sequence identity, based on the Clustal V method of alignment, when compared to SEQ ID NO:4, or
   (b) a complement of the nucleotide sequence, wherein the complement and the nucleotide sequence consist of the same number of nucleotides and are 100% complementary.

2. The polynucleotide of claim 1, wherein the amino acid sequence of the polypeptide comprises SEQ ID NO:4.

3. The polynucleotide of claim 1 wherein the nucleotide sequence comprises SEQ ID NO:3.

4. A vector comprising the polynucleotide of claim 1.

5. A recombinant DNA construct comprising the polynucleotide of claim 1 operably linked to at least one regulatory sequence.

6. A method for transforming a cell, comprising transforming a cell with the polynucleotide of claim 1.

7. A cell comprising the recombinant DNA construct of claim 5.

8. A method for producing a plant comprising transforming a plant cell with the polynucleotide of claim 1 and regenerating a plant from the transformed plant cell.

9. A plant comprising the recombinant DNA construct of claim 5.

10. A seed comprising the recombinant DNA construct of claim 5.

11. A method for production of a polypeptide having sulfite reductase activity comprising the steps of cultivating the cell of claim 7 under conditions that allow for the synthesis of the polypeptide and isolating the polypeptide from the cultivated cells, from culture medium, or from both the cultivated cells and the culture medium.

* * * * *

SEQUENCE LISTING

<160> NUMBER OF SEQ ID NOS: 8

<210> SEQ ID NO 1
<211> LENGTH: 2327
<212> TYPE: DNA
<213> ORGANISM: Oryza sativa

<400> SEQUENCE: 1

```
gcacgaggaa gaggaaatat cccactcgct tcgacactct cttcccttc ttctcccgga      60
gaaaacctcg agccaaggcc ccgactccga ctccggtgat gtcggcggcg gtgggggag    120
ccgagttcca cgggttccgt gggggtggcg gcggcgcggc gcagctgcag aggtcgcgga   180
tgctcggaag gccgctccgt gtggcgaccc ctcacgcggc ggccccgct ggcggcggcg    240
ggtcgtcgtc ggccagcata cgcgccgtct ccgcgccact caagaaggat gcatctgaag   300
ttaagaggag caaggttgag atcatcaagg agaagagcaa ttttcttcgg taccctttga   360
atgaggaact ggtctcagag gctcccaata ttaatgacga cgctgtccag cttattaaat   420
ttcatggaag ctatcaacag acggaccgtg atgttcgtgg gcagaagaat tactcgttta   480
tgctccgaac aaagaatcct tgtggaaaag ttccaaacca gctttacttg gctatggata   540
cgctagctga tgaatttggt attggaacac tccgattgac gaccagacaa acatttcagc   600
tgcatggcgt tcttaagaag aacctgaaga ctgtcatcag cactgttata agaatatgg    660
gttcatcatt aggtgcctgt ggagatctca acagaaatgt acttgcacct gcagcaccttt  720
atgtcaggaa ggatattctt tttgctcaag aaacagcaga gaatatcgca gctcttctta   780
caccacaatc tgggcttat tatgacctgt gggtggatgg agaaaagata atgtcagccg    840
aagaacctcc tgaggtcacg aaagctcgca atgacaacac atatggaaca aatttccccg   900
attcccctga accaatatat ggcacacagt atctgccaag aaagttcaag attgctgtca   960
ctgtcgctgg agataactct gttgatattc tgaccaatga catcggtgtt gttgttgttt  1020
cagatagtgc aggagagcct gttggcttca acatttatgt tggtggtggc atgggtagga   1080
cacaccgagt ggagaccaca ttccctcgat tggctgatcc actgggttat gttcctaagg   1140
aagatatatt gtatgctata aaagcaatag tcgtcacaca gagggaaaat gggagaaggg   1200
atgaccgccg atatagcagg atgaagtatc tgattgataa ctggggaatt gagaagtttc   1260
gggctgaagt cgaaaaatac tatggaaaga gtttgaaga ttctcgtcct ttgcccgaat    1320
ggcagttcaa cagctaccta ggatggcagg aacagggtga tggaaaatta ttctacggag   1380
tgcatgttga taatggtcgt gtcgcagggc aagcaaagaa aactctacga gagattattg   1440
agaagtacaa tttggaagtt agcattactc caaaccagaa tcttatctta tgtgggattg   1500
atcaagcatg gaaagatccc atcacagcag ctcttgctca atctggcctg ctggaaccaa   1560
aggatgttga tcccctgaat attacttcca tggcatgtcc tgccttacca ctgtgccctc   1620
tagcacaaac agaagctgaa cgagggattc tgccgattct taaacgaatt agagcagttt   1680
```

-continued

```
ttgataaggt tggcatcaag gaccatgagt cggtagtggt gaggataaca ggctgcccta    1740
atggatgcgc tagaccatat atggcagagg ttggctttgt tggtgatggc ccaaacagtt    1800
accagatatg gcttggagga acaccaaacc agagtaccct agctgaaacc tttatgaata    1860
aagtgaagct tcaagatatt gagaaggttt tggaaccatt gttttcctat tggaacagca    1920
cacgtcagga aggtgaatct tttggtagct tcacacgccg gacgggattt gacaaattga    1980
aagaggtagt gaacaagtgg gcagagtcag catcagctgc atgatggact gctttcgctg    2040
aacaagttga taacaattct gaccacgggt ccaatgcggg catcgtcaag ggctctcaac    2100
ataactatgt gagcattgca ggagaaaatt ttgtcaattt cgttgacaag attgaggact    2160
cgccgactcg ggtttggaat cgttcgttca gataattaat caaaattttt cgtgtactct    2220
ggtttgagaa aaaaaaatgt gcttatgaga aaacaaaagg aaccctggct gtttactttg    2280
gaataaattg cttggaaagt gtactgaata aaaaaaaaaa aaaaaaa                  2327
```

<210> SEQ ID NO 2
<211> LENGTH: 673
<212> TYPE: PRT
<213> ORGANISM: Oryza sativa

<400> SEQUENCE: 2

```
Thr Arg Lys Arg Lys Tyr Pro Thr Arg Phe Asp Thr Leu Phe Pro Phe
  1               5                  10                  15

Phe Ser Arg Arg Lys Pro Arg Ala Lys Ala Pro Thr Pro Thr Pro Val
             20                  25                  30

Met Ser Ala Ala Val Gly Gly Ala Glu Phe His Gly Phe Arg Gly Gly
         35                  40                  45

Gly Gly Gly Ala Ala Gln Leu Gln Arg Ser Arg Met Leu Gly Arg Pro
     50                  55                  60

Leu Arg Val Ala Thr Pro His Ala Ala Pro Ala Gly Gly Gly Gly
 65                  70                  75                  80

Ser Ser Ser Ala Ser Ile Arg Ala Val Ser Ala Pro Leu Lys Lys Asp
             85                  90                  95

Ala Ser Glu Val Lys Arg Ser Lys Val Glu Ile Ile Lys Glu Lys Ser
            100                 105                 110

Asn Phe Leu Arg Tyr Pro Leu Asn Glu Glu Leu Val Ser Glu Ala Pro
        115                 120                 125

Asn Ile Asn Asp Ser Ala Val Gln Leu Ile Lys Phe His Gly Ser Tyr
    130                 135                 140

Gln Gln Thr Asp Arg Asp Val Arg Gly Gln Lys Asn Tyr Ser Phe Met
145                 150                 155                 160

Leu Arg Thr Lys Asn Pro Cys Gly Lys Val Pro Asn Gln Leu Tyr Leu
                165                 170                 175

Ala Met Asp Thr Leu Ala Asp Glu Phe Gly Ile Gly Thr Leu Arg Leu
            180                 185                 190

Thr Thr Arg Gln Thr Phe Gln Leu His Gly Val Leu Lys Lys Asn Leu
        195                 200                 205

Lys Thr Val Ile Ser Thr Val Ile Lys Asn Met Gly Ser Ser Leu Gly
    210                 215                 220

Ala Cys Gly Asp Leu Asn Arg Asn Val Leu Ala Pro Ala Pro Tyr
225                 230                 235                 240

Val Arg Lys Asp Ile Leu Phe Ala Gln Glu Thr Ala Glu Asn Ile Ala
                245                 250                 255
```

-continued

```
Ala Leu Leu Thr Pro Gln Ser Gly Ala Tyr Tyr Asp Leu Trp Val Asp
            260                 265                 270

Gly Glu Lys Ile Met Ser Ala Glu Glu Pro Glu Val Thr Lys Ala
        275                 280                 285

Arg Asn Asp Asn Thr Tyr Gly Thr Asn Phe Pro Asp Ser Pro Glu Pro
        290                 295                 300

Ile Tyr Gly Thr Gln Tyr Leu Pro Arg Lys Phe Lys Ile Ala Val Thr
305                 310                 315                 320

Val Ala Gly Asp Asn Ser Val Asp Ile Leu Thr Asn Asp Ile Gly Val
                325                 330                 335

Val Val Val Ser Asp Ser Ala Gly Glu Pro Val Gly Phe Asn Ile Tyr
            340                 345                 350

Val Gly Gly Gly Met Gly Arg Thr His Arg Val Glu Thr Thr Phe Pro
            355                 360                 365

Arg Leu Ala Asp Pro Leu Gly Tyr Val Pro Lys Glu Asp Ile Leu Tyr
        370                 375                 380

Ala Ile Lys Ala Ile Val Val Thr Gln Arg Glu Asn Gly Arg Arg Asp
385                 390                 395                 400

Asp Arg Arg Tyr Ser Arg Met Lys Tyr Leu Ile Asp Asn Trp Gly Ile
                405                 410                 415

Glu Lys Phe Arg Ala Glu Val Glu Lys Tyr Tyr Gly Lys Lys Phe Glu
                420                 425                 430

Asp Ser Arg Pro Leu Pro Glu Trp Gln Phe Asn Ser Tyr Leu Gly Trp
            435                 440                 445

Gln Glu Gln Gly Asp Gly Lys Leu Phe Tyr Gly Val His Val Asp Asn
        450                 455                 460

Gly Arg Val Ala Gly Gln Ala Lys Lys Thr Leu Arg Glu Ile Ile Glu
465                 470                 475                 480

Lys Tyr Asn Leu Glu Val Ser Ile Thr Pro Asn Gln Asn Leu Ile Leu
                485                 490                 495

Cys Gly Ile Asp Gln Ala Trp Lys Asp Pro Ile Thr Ala Ala Leu Ala
            500                 505                 510

Gln Ser Gly Leu Leu Glu Pro Lys Asp Val Asp Pro Leu Asn Ile Thr
        515                 520                 525

Ser Met Ala Cys Pro Ala Leu Pro Leu Cys Pro Leu Ala Gln Thr Glu
        530                 535                 540

Ala Glu Arg Gly Ile Leu Pro Ile Leu Lys Arg Ile Arg Ala Val Phe
545                 550                 555                 560

Asp Lys Val Gly Ile Lys Asp His Glu Ser Val Val Arg Ile Thr
                565                 570                 575

Gly Cys Pro Asn Gly Cys Ala Arg Pro Tyr Met Ala Glu Val Gly Phe
            580                 585                 590

Val Gly Asp Gly Pro Asn Ser Tyr Gln Ile Trp Leu Gly Gly Thr Pro
        595                 600                 605

Asn Gln Ser Thr Leu Ala Glu Thr Phe Met Asn Lys Val Lys Leu Gln
        610                 615                 620

Asp Ile Glu Lys Val Leu Glu Pro Leu Phe Ser Tyr Trp Asn Ser Thr
625                 630                 635                 640

Arg Gln Glu Gly Glu Ser Phe Gly Ser Phe Thr Arg Arg Thr Gly Phe
                645                 650                 655

Asp Lys Leu Lys Glu Val Val Asn Lys Trp Ala Glu Ser Ala Ser Ala
            660                 665                 670

Ala
```

<210> SEQ ID NO 3
<211> LENGTH: 2408
<212> TYPE: DNA
<213> ORGANISM: Glycine max

<400> SEQUENCE: 3

```
tgatgacgac gtcttttgga ccagccacca cctcagcgcc gcttaaggac cacaaagttc      60
agatcccaag cttccatggc ttgaggtctt cctccgcctc tgctctcccc cgcaatgccc     120
tctcccttcc ttcatccact cgctctctct ccctcatacg tgctgtttcc acgcctgcgc     180
agtctgaaac tgccactgtc aagcgcagca agtcgaaat  attcaaagaa caaagcaatt     240
tcataagata tcctcttaac gaggacattt tgacggatgc tcctaatata agtgaagccg     300
ccactcaatt gatcaagttt catggtagct atcaacagta caatagagag gagcgtggtt     360
ccagaagcta ctctttcatg atacgcacta agaatccatg cgggaaggtt ccaaccaac      420
tttacctcac catggatgat cttgctgacc agtttgggat tgggacgctt cgcttgacca     480
ccaggcagac gtttcagctc catggtgttc tcaagaagga ccttaaaaca gtcatgggta     540
ccattattag gaacatgggc tcgactcttg gtgcttgtgg cgacctaaac aggaatgtgc     600
ttgctcctgc agctcccctt gcaagaaaag attacctctt tgctcaacaa actgctgaga     660
acattgctgc gctcctcgct cctcagtctg gtttctacta tgatatttgg gtggatgggg     720
aaaagatttt gacatcagaa ccacctgaag tagttcaggc acgaaatgac aattctcatg     780
gtacaaactt cccggattcc cccgagccca tctatggaac tcagttcttg ccaaggaaat     840
tcaaaattgc tgttactgtg ccaactgata actccgtgga cattctcaca aatgatattg     900
gtgttgttgt tgttaccgat gacgatgggg agcctcaagg gttcaacata tatgttggtg     960
gtggaatggg aagaactcat aggttggaaa ccacttttcc tcgcttggca gaaccaatag    1020
gttacgtacc aaaggaggat attttgtatg cagtgaaagc aattgttgtt acacaacgag    1080
aaaatgggag aagagatgac cgcaagtata gtagattgaa atatttgata agctcttggg    1140
gaattgaaaa gtttagaagt gtagttgagc aatattatgg caagaaattt gaacctttcc    1200
gtgcattgcc agaatgggaa tttaaaagtt atcttgggtg gcatgaacag ggcgatggca    1260
aactttttta tggtcttcat gttgataatg gtcgtattgg tggaaacatg aaaaagacat    1320
tgagggaggt tatcgagaag tataatttga atgtaagaat cactccaaat cagaatatca    1380
tcttgactga tgttcgtgct gcatggaagc gtcccattac aaccacgctt gctcaagctg    1440
gtttgctgca acctagattt gtagatcccc tcaacataac agcaatggca tgccctgctt    1500
tcccattatg tcctctggca attactgaag ctgaacgtgg gatacctaac atacttaagc    1560
ggattcgtga tgttttttgat aaggttggcc tgaagtatag tgagtctgtg gttgtaagga    1620
taactggctg ccctaatggt tgtgctagac atacatggcc tgaacttgga ctagttggtg    1680
atggtccaaa tagctatcag atttggcttg gaggaaacca taaacaaaca tcattagctc    1740
gaagtttcat ggacagggtg aagattctag accttgaaaa agttttggag cctttgtttt    1800
attattggaa gcaaaagcgt caatctaaag aatcatttgg tgacttcaca aaccgaatgg    1860
gatttgagaa gcttaaagaa tatattgaga atgggaggg  tccagtggta gcaccatcac    1920
gccacaacct caagcttttt gctgacaagg agacatatga atcaatggat gcattagcaa    1980
agcttcaaaa caagactgct catcagttgg ccatggaagt tatccgtaat tatgttgctt    2040
ccaaccaaaa tggaaaaggc gaatgatttc attttttactt aacgaaggaa gatgtatgtg    2100
```

-continued

```
atgttgcttt atggttgaca ggaatggtgg ataggcaact gaacacaact ctgttgttac   2160
tgtgtggtaa ctcgggttcg actaaactaa tgtttgggtt tttgtttttt tatctgaaac   2220
ggctttccgt agaatctttt ggttcatcat ttagatcgag tttctgaaca taaataagc    2280 ctttctgtca tttctgtatc caattttggg tgttcgacag cttggttttt cttcacaata   2340
atcttgctag ccaagaccct tttccgattt tgcgcttgct ccaataaagt tcattaatca   2400
ggatttgt                                                             2408
```

<210> SEQ ID NO 4
<211> LENGTH: 687
<212> TYPE: PRT
<213> ORGANISM: Glycine max

<400> SEQUENCE: 4

```
Met Thr Thr Ser Phe Gly Pro Ala Thr Thr Ser Ala Pro Leu Lys Asp
  1               5                  10                  15

His Lys Val Gln Ile Pro Ser Phe His Gly Leu Arg Ser Ser Ser Ala
             20                  25                  30

Ser Ala Leu Pro Arg Asn Ala Leu Ser Leu Pro Ser Ser Thr Arg Ser
         35                  40                  45

Leu Ser Leu Ile Arg Ala Val Ser Thr Pro Ala Gln Ser Glu Thr Ala
     50                  55                  60

Thr Val Lys Arg Ser Lys Val Glu Ile Phe Lys Glu Gln Ser Asn Phe
 65                  70                  75                  80

Ile Arg Tyr Pro Leu Asn Glu Asp Ile Leu Thr Asp Ala Pro Asn Ile
                 85                  90                  95

Ser Glu Ala Ala Thr Gln Leu Ile Lys Phe His Gly Ser Tyr Gln Gln
            100                 105                 110

Tyr Asn Arg Glu Glu Arg Gly Ser Arg Ser Tyr Ser Phe Met Ile Arg
        115                 120                 125

Thr Lys Asn Pro Cys Gly Lys Val Ser Asn Gln Leu Tyr Leu Thr Met
    130                 135                 140

Asp Asp Leu Ala Asp Gln Phe Gly Ile Gly Thr Leu Arg Leu Thr Thr
145                 150                 155                 160

Arg Gln Thr Phe Gln Leu His Gly Val Leu Lys Lys Asp Leu Lys Thr
                165                 170                 175

Val Met Gly Thr Ile Ile Arg Asn Met Gly Ser Thr Leu Gly Ala Cys
            180                 185                 190

Gly Asp Leu Asn Arg Asn Val Leu Ala Pro Ala Pro Leu Ala Arg
        195                 200                 205

Lys Asp Tyr Leu Phe Ala Gln Gln Thr Ala Glu Asn Ile Ala Ala Leu
    210                 215                 220

Leu Ala Pro Gln Ser Gly Phe Tyr Tyr Asp Ile Trp Val Asp Gly Glu
225                 230                 235                 240

Lys Ile Leu Thr Ser Glu Pro Pro Glu Val Val Gln Ala Arg Asn Asp
                245                 250                 255

Asn Ser His Gly Thr Asn Phe Pro Asp Ser Pro Glu Pro Ile Tyr Gly
            260                 265                 270

Thr Gln Phe Leu Pro Arg Lys Phe Lys Ile Ala Val Thr Val Pro Thr
        275                 280                 285

Asp Asn Ser Val Asp Ile Leu Thr Asn Asp Ile Gly Val Val Val
    290                 295                 300

Thr Asp Asp Asp Gly Glu Pro Gln Gly Phe Asn Ile Tyr Val Gly Gly
305                 310                 315                 320
```

```
Gly Met Gly Arg Thr His Arg Leu Glu Thr Thr Phe Pro Arg Leu Ala
            325                 330                 335

Glu Pro Ile Gly Tyr Val Pro Lys Glu Asp Ile Leu Tyr Ala Val Lys
            340                 345                 350

Ala Ile Val Val Thr Gln Arg Glu Asn Gly Arg Arg Asp Asp Arg Lys
            355                 360                 365

Tyr Ser Arg Leu Lys Tyr Leu Ile Ser Ser Trp Gly Ile Glu Lys Phe
        370                 375                 380

Arg Ser Val Val Glu Gln Tyr Tyr Gly Lys Lys Phe Glu Pro Phe Arg
385                 390                 395                 400

Ala Leu Pro Glu Trp Glu Phe Lys Ser Tyr Leu Gly Trp His Glu Gln
            405                 410                 415

Gly Asp Gly Lys Leu Phe Tyr Gly Leu His Val Asp Asn Gly Arg Ile
            420                 425                 430

Gly Gly Asn Met Lys Lys Thr Leu Arg Glu Val Ile Glu Lys Tyr Asn
            435                 440                 445

Leu Asn Val Arg Ile Thr Pro Asn Gln Asn Ile Ile Leu Thr Asp Val
        450                 455                 460

Arg Ala Ala Trp Lys Arg Pro Ile Thr Thr Leu Ala Gln Ala Gly
465                 470                 475                 480

Leu Leu Gln Pro Arg Phe Val Asp Pro Leu Asn Ile Thr Ala Met Ala
            485                 490                 495

Cys Pro Ala Phe Pro Leu Cys Pro Leu Ala Ile Thr Glu Ala Glu Arg
            500                 505                 510

Gly Ile Pro Asn Ile Leu Lys Arg Ile Arg Asp Val Phe Asp Lys Val
            515                 520                 525

Gly Leu Lys Tyr Ser Glu Ser Val Val Arg Ile Thr Gly Cys Pro
        530                 535                 540

Asn Gly Cys Ala Arg Pro Tyr Met Ala Glu Leu Gly Leu Val Gly Asp
545                 550                 555                 560

Gly Pro Asn Ser Tyr Gln Ile Trp Leu Gly Gly Asn His Lys Gln Thr
            565                 570                 575

Ser Leu Ala Arg Ser Phe Met Asp Arg Val Lys Ile Leu Asp Leu Glu
            580                 585                 590

Lys Val Leu Glu Pro Leu Phe Tyr Tyr Trp Lys Gln Lys Arg Gln Ser
        595                 600                 605

Lys Glu Ser Phe Gly Asp Phe Thr Asn Arg Met Gly Phe Glu Lys Leu
    610                 615                 620

Lys Glu Tyr Ile Glu Lys Trp Glu Gly Pro Val Val Ala Pro Ser Arg
625                 630                 635                 640

His Asn Leu Lys Leu Phe Ala Asp Lys Glu Thr Tyr Glu Ser Met Asp
            645                 650                 655

Ala Leu Ala Lys Leu Gln Asn Lys Thr Ala His Gln Leu Ala Met Glu
            660                 665                 670

Val Ile Arg Asn Tyr Val Ala Ser Asn Gln Asn Gly Lys Gly Glu
            675                 680                 685
```

<210> SEQ ID NO 5
<211> LENGTH: 1152
<212> TYPE: DNA
<213> ORGANISM: Triticum aestivum

<400> SEQUENCE: 5
ggcgatagtt gttacacaga gggaaaatgg aagaagagat gaccgcaggt atagcagact    60

```
gaagtatctg cttgacagct ggggaattga caagtttcgg gccgaagctg aaaaatacta    120
tgggaagaag tttgaagatt ccgcccatt gccggaatgg cagttcaaca gctaccttgg    180
gtggcaggag cagggtgatg gtaaattatt ctatggagtg catgttgata atggtcgtct    240 tgggggcaa gcaaagaaaa ctctgcgaga gataattgag aagtatagct tggatgttag    300
tattactcca aaccaaaacc ttatcttatg tggggttgat caggcatgga gagaacccat    360
aactgcagct cttgctcaag ctggcctgtt ggaaccaaag gatgttgatc tcctgaacat    420
aacctccatg gcatgccctg ccttacctct gtgccctcta gcacaaacag aagctgaacg    480
agggatcctg ccaattctta aacgaattag agcagttttt gacaaggttg gtatcaagga    540
tgaggagtct gtagtggtga ggataactgg ctgccccaat ggatgcgcca gaccatatat    600
ggcagaggtt ggctttgttg gtgacggccc aaacagctac cagatatggc ttggaggaac    660
accaaaccag accaccttgg cagagacgtt tatgaataaa gtgaagcttc aagatattga    720
gaaagttttg gaaccactgt tttcctattg gaatagcacg cgccaggaag gcgaatcctt    780
tggaagcttc acaaaccgaa tgggatttga gcaactgaag gaggtggtga acaagtggga    840
ggggtcagcg tcagccgcat gagagttgtc tttgctggac aaatcccagc accattttg    900 ctggggtgag aatctggtgg cgaccaatta ctccacggat tactttata taaaaactta    960 ggagaggagg aggaaacctg tcaattccgt tgacaggcgg aggacgaaga aagagccggg   1020
tctgaagaag ttgctccttt gtgtttgttg tgaggtttta ttttttttgtg tgtacttgta   1080 tggataactc cgttggcccc tttgtttagc ctgagaataa attccttgca aaaaaaaaaa   1140
aaaaaaaaaa aa                                                       1152
```

<210> SEQ ID NO 6
<211> LENGTH: 286
<212> TYPE: PRT
<213> ORGANISM: Triticum aestivum

<400> SEQUENCE: 6

```
Ala Ile Val Val Thr Gln Arg Glu Asn Gly Arg Arg Asp Asp Arg Arg
 1               5                  10                  15

Tyr Ser Arg Leu Lys Tyr Leu Leu Asp Ser Trp Gly Ile Asp Lys Phe
            20                  25                  30

Arg Ala Glu Ala Glu Lys Tyr Tyr Gly Lys Lys Phe Glu Asp Phe Arg
        35                  40                  45

Pro Leu Pro Glu Trp Gln Phe Asn Ser Tyr Leu Gly Trp Gln Glu Gln
    50                  55                  60

Gly Asp Gly Lys Leu Phe Tyr Gly Val His Val Asp Asn Gly Arg Leu
65                  70                  75                  80

Gly Gly Gln Ala Lys Lys Thr Leu Arg Glu Ile Ile Glu Lys Tyr Ser
                85                  90                  95

Leu Asp Val Ser Ile Thr Pro Asn Gln Asn Leu Ile Leu Cys Gly Val
           100                 105                 110

Asp Gln Ala Trp Arg Glu Pro Ile Thr Ala Ala Leu Ala Gln Ala Gly
       115                 120                 125

Leu Leu Glu Pro Lys Asp Val Asp Leu Leu Asn Ile Thr Ser Met Ala
   130                 135                 140

Cys Pro Ala Leu Pro Leu Cys Pro Leu Ala Gln Thr Glu Ala Glu Arg
145                 150                 155                 160

Gly Ile Leu Pro Ile Leu Lys Arg Ile Arg Ala Val Phe Asp Lys Val
               165                 170                 175
```

```
Gly Ile Lys Asp Glu Glu Ser Val Val Arg Ile Thr Gly Cys Pro
            180                 185                 190
Asn Gly Cys Ala Arg Pro Tyr Met Ala Glu Val Gly Phe Val Gly Asp
        195                 200                 205
Gly Pro Asn Ser Tyr Gln Ile Trp Leu Gly Gly Thr Pro Asn Gln Thr
        210                 215                 220
Thr Leu Ala Glu Thr Phe Met Asn Lys Val Lys Leu Gln Asp Ile Glu
225                 230                 235                 240
Lys Val Leu Glu Pro Leu Phe Ser Tyr Trp Asn Ser Thr Arg Gln Glu
                245                 250                 255
Gly Glu Ser Phe Gly Ser Phe Thr Asn Arg Met Gly Phe Glu Gln Leu
                260                 265                 270
Lys Glu Val Val Asn Lys Trp Glu Gly Ser Ala Ser Ala Ala
                275                 280                 285

<210> SEQ ID NO 7
<211> LENGTH: 635
<212> TYPE: PRT
<213> ORGANISM: Zea mays

<400> SEQUENCE: 7

Met Ser Gly Ala Ile Gly Gly Ala Glu Val His Gly Phe Arg Gly Ala
1               5                   10                  15
Ala Ala Gln Leu Pro Arg Ser Arg Val Leu Gly Arg Pro Ile Arg Val
                20                  25                  30
Ala Pro Pro Ala Ala Ala Arg Pro Gly Gly Ala Ser Ala Gly Ser Ile
            35                  40                  45
Arg Ala Val Ser Ala Pro Ala Lys Lys Asp Ala Ser Glu Val Lys Arg
        50                  55                  60
Ser Lys Val Glu Ile Ile Lys Glu Lys Ser Asn Phe Leu Arg Tyr Pro
65                  70                  75                  80
Leu Asn Glu Glu Leu Val Ser Glu Ala Pro Asn Ile Asn Glu Ser Ala
                85                  90                  95
Val Gln Leu Ile Lys Phe His Gly Ser Tyr Gln Gln Thr Asp Arg Asp
                100                 105                 110
Val Arg Gly Gln Lys Asn Tyr Ser Phe Met Leu Arg Thr Lys Asn Pro
            115                 120                 125
Cys Gly Lys Val Pro Asn Gln Leu Tyr Leu Ala Met Asp Thr Leu Ala
        130                 135                 140
Asp Glu Phe Gly Ile Gly Thr Leu Arg Leu Thr Thr Arg Gln Thr Phe
145                 150                 155                 160
Gln Leu His Gly Val Leu Lys Lys Asn Leu Lys Thr Val Leu Ser Thr
                165                 170                 175
Val Ile Lys Asn Met Gly Ser Thr Leu Gly Ala Cys Gly Asp Leu Asn
                180                 185                 190
Arg Asn Val Leu Ala Pro Ala Pro Tyr Val Lys Lys Asp Ile Leu
            195                 200                 205
Phe Ala Gln Gln Thr Ala Glu Asn Ile Ala Ala Leu Leu Thr Pro Gln
        210                 215                 220
Ser Gly Ala Tyr Tyr Asp Leu Trp Val Asp Gly Glu Lys Ile Met Ser
225                 230                 235                 240
Ala Glu Glu Pro Pro Glu Val Thr Lys Ala Arg Asn Asp Asn Ser His
                245                 250                 255
Gly Thr Asn Phe Pro Asp Ser Pro Glu Pro Ile Tyr Gly Thr Gln Tyr
```

-continued

```
                     260                 265                 270
Leu Pro Arg Lys Phe Lys Val Ala Val Thr Ala Ala Gly Asp Asn Ser
                275                 280                 285
Val Asp Ile Leu Thr Asn Asp Ile Gly Val Val Val Ser Asp Asp
    290                 295                 300
Ala Gly Glu Pro Ile Gly Phe Asn Ile Tyr Val Gly Gly Met Gly
305                 310                 315                 320
Arg Thr His Arg Val Glu Thr Thr Phe Pro Arg Leu Ala Asp Pro Leu
                325                 330                 335
Gly Tyr Val Pro Lys Glu Asp Ile Leu Tyr Ala Ile Lys Ala Ile Val
                340                 345                 350
Val Thr Gln Arg Glu Asn Gly Arg Arg Asp Asp Arg Lys Tyr Ser Arg
            355                 360                 365
Met Lys Tyr Met Ile Asp Arg Trp Gly Ile Asp Arg Phe Arg Ala Glu
        370                 375                 380
Val Glu Lys Tyr Tyr Gly Lys Lys Phe Glu Ser Phe Arg Pro Leu Pro
385                 390                 395                 400
Glu Trp Gln Phe Asn Ser Tyr Leu Gly Trp Gln Glu Gln Gly Asp Gly
                405                 410                 415
Lys Leu Phe Tyr Gly Val His Val Asp Asn Gly Arg Val Gly Gly Gln
                420                 425                 430
Ala Lys Lys Thr Leu Arg Glu Ile Ile Glu Lys Tyr Asn Leu Asp Val
            435                 440                 445
Ser Ile Thr Pro Asn Gln Asn Leu Ile Leu Cys Gly Ile Asp Gln Ala
        450                 455                 460
Trp Arg Glu Pro Ile Thr Thr Ala Leu Ala Gln Ala Gly Leu Leu Glu
465                 470                 475                 480
Pro Lys Asp Val Asp Pro Leu Asn Leu Thr Ala Met Ala Cys Pro Ala
                485                 490                 495
Leu Pro Leu Cys Pro Leu Ala Gln Thr Glu Ala Glu Arg Gly Ile Leu
                500                 505                 510
Pro Ile Leu Lys Arg Ile Arg Ala Val Phe Asn Lys Val Gly Ile Lys
            515                 520                 525
Asp Ser Glu Ser Val Val Arg Ile Thr Gly Cys Pro Asn Gly Cys
        530                 535                 540
Ala Arg Pro Tyr Met Ala Glu Leu Gly Phe Val Gly Asp Gly Pro Lys
545                 550                 555                 560
Ser Tyr Gln Ile Trp Leu Gly Gly Thr Pro Asn Gln Ser Thr Leu Ala
                565                 570                 575
Glu Ser Phe Met Asp Lys Val Lys Leu Asp Asp Ile Glu Lys Val Leu
                580                 585                 590
Glu Pro Leu Phe Thr Tyr Trp Asn Gly Thr Arg Gln Glu Gly Glu Ser
            595                 600                 605
Phe Gly Ser Phe Thr Asn Arg Thr Gly Phe Asp Lys Leu Lys Glu Val
        610                 615                 620
Val Asn Lys Trp Ala Glu Ser Pro Ser Ala Ala
625                 630                 635

<210> SEQ ID NO 8
<211> LENGTH: 693
<212> TYPE: PRT
<213> ORGANISM: Nicotiana tabacum

<400> SEQUENCE: 8
```

-continued

```
Met Thr Thr Ser Phe Gly Ala Ala Ile Asn Ile Ala Val Ala Asp Asp
 1               5                  10                  15

Pro Asn Pro Lys Leu Gln Ile His Asn Phe Ser Gly Leu Lys Ser Thr
            20                  25                  30

Ser Asn Ser Leu Leu Leu Ser Arg Arg Leu His Val Phe Gln Ser Phe
        35                  40                  45

Ser Pro Ser Asn Pro Ser Ser Ile Val Arg Ala Val Ser Thr Pro Ala
50                  55                  60

Lys Pro Ala Ala Val Glu Pro Lys Arg Ser Lys Val Glu Ile Phe Lys
65                  70                  75                  80

Glu Gln Ser Asn Phe Ile Arg Tyr Pro Leu Asn Glu Ile Leu Asn
                85                  90                  95

Asp Ala Pro Asn Ile Asn Glu Ala Ala Thr Gln Leu Ile Lys Phe His
            100                 105                 110

Gly Ser Tyr Met Gln Tyr Asp Arg Asp Glu Arg Gly Gly Arg Ser Tyr
        115                 120                 125

Ser Phe Met Leu Arg Thr Lys Asn Pro Gly Gly Glu Val Pro Asn Arg
130                 135                 140

Leu Tyr Leu Val Met Asp Asp Leu Ala Asp Gln Phe Gly Ile Gly Thr
145                 150                 155                 160

Leu Arg Leu Thr Thr Arg Gln Thr Phe Gln Leu His Gly Val Leu Lys
                165                 170                 175

Lys Asn Leu Lys Thr Val Met Ser Thr Ile Ile Lys Asn Met Gly Ser
            180                 185                 190

Thr Leu Gly Ala Cys Gly Asp Leu Asn Arg Asn Val Leu Ala Pro Ala
        195                 200                 205

Ala Pro Phe Ala Lys Lys Asp Tyr Met Phe Ala Lys Gln Thr Ala Asp
    210                 215                 220

Asn Ile Ala Ala Leu Leu Thr Pro Gln Ser Gly Phe Tyr Tyr Asp Val
225                 230                 235                 240

Trp Val Asp Gly Glu Lys Val Met Thr Ala Glu Pro Pro Glu Val Val
                245                 250                 255

Lys Ala Arg Asn Asp Asn Ser His Gly Thr Asn Phe Pro Asp Ser Pro
            260                 265                 270

Glu Pro Ile Tyr Gly Thr Gln Phe Leu Pro Arg Lys Phe Lys Ile Ala
        275                 280                 285

Val Thr Val Pro Thr Asp Asn Ser Val Asp Ile Phe Thr Asn Asp Ile
    290                 295                 300

Gly Val Val Val Ser Asn Glu Asp Gly Glu Pro Gln Gly Phe Asn
305                 310                 315                 320

Ile Tyr Val Gly Gly Met Gly Arg Thr His Arg Met Glu Thr Thr
                325                 330                 335

Phe Pro Arg Leu Ala Glu Pro Leu Gly Tyr Val Pro Lys Glu Asp Ile
            340                 345                 350

Leu Tyr Ala Val Lys Ala Ile Val Val Thr Gln Arg Glu Asn Gly Arg
        355                 360                 365

Arg Asp Asp Arg Arg Tyr Ser Arg Leu Lys Tyr Leu Leu Ser Ser Trp
370                 375                 380

Gly Ile Glu Lys Phe Arg Ser Val Thr Glu Gln Tyr Tyr Gly Lys Lys
385                 390                 395                 400

Phe Gln Pro Cys Arg Glu Leu Pro Glu Trp Glu Phe Lys Ser Tyr Leu
            405                 410                 415

Gly Trp His Glu Ala Gly Asp Gly Ser Leu Phe Cys Gly Leu His Val
```

-continued

```
                         420                 425                 430
Asp Asn Gly Arg Val Lys Gly Ala Met Lys Lys Ala Leu Arg Glu Val
        435                 440                 445
Ile Glu Lys Tyr Asn Leu Asn Val Arg Leu Thr Pro Asn Gln Asn Ile
    450                 455                 460
Ile Leu Cys Asn Ile Arg Gln Ala Trp Lys Arg Pro Ile Thr Thr Val
465                 470                 475                 480
Leu Ala Gln Gly Gly Leu Leu Gln Pro Arg Tyr Val Asp Pro Leu Asn
                485                 490                 495
Leu Thr Ala Met Ala Cys Pro Ala Phe Pro Leu Cys Pro Leu Ala Ile
                500                 505                 510
Thr Glu Ala Glu Arg Gly Ile Pro Asp Ile Leu Lys Arg Val Arg Ala
            515                 520                 525
Ile Phe Glu Arg Val Gly Leu Lys Tyr Ser Glu Ser Val Val Ile Arg
        530                 535                 540
Ile Thr Gly Cys Pro Asn Gly Cys Ala Arg Pro Tyr Met Ala Glu Leu
545                 550                 555                 560
Gly Leu Val Gly Asp Gly Pro Asn Ser Tyr Gln Ile Trp Leu Gly Gly
                565                 570                 575
Thr Pro Asn Gln Thr Ser Leu Ala Lys Thr Phe Lys Asp Lys Leu Lys
                580                 585                 590
Val Gln Asp Leu Glu Lys Val Leu Glu Pro Leu Phe Phe His Trp Arg
            595                 600                 605
Arg Lys Arg Gln Ser Lys Glu Ser Phe Gly Asp Phe Thr Asn Arg Met
        610                 615                 620
Gly Phe Glu Lys Leu Gly Glu Phe Val Glu Lys Trp Glu Gly Ile Pro
625                 630                 635                 640
Glu Ser Ser Arg Tyr Asn Leu Lys Leu Phe Ala Asp Arg Glu Thr
                645                 650                 655
Tyr Glu Ala Met Asp Ala Leu Ala Ser Ile Gln Asp Lys Asn Ala His
                660                 665                 670
Gln Leu Ala Ile Glu Val Val Arg Asn Tyr Val Ala Ser Gln Gln Asn
            675                 680                 685
Gly Lys Ser Met Asp
    690
```